US011116769B2

(12) United States Patent
Jeon et al.

(10) Patent No.: US 11,116,769 B2
(45) Date of Patent: Sep. 14, 2021

(54) TADALAFIL FREE BASE-CONTAINING FILM DOSAGE FORM CONTAINING POLYETHYLENE GLYCOL-BASED POLYMER AND/OR VINYL PYRROLIDONE-BASED POLYMER AS DISPERSION STABILIZER

(71) Applicant: CTC BIO, INC., Seoul (KR)

(72) Inventors: Hong Ryeol Jeon, Suwon-si (KR);
Do-Woo Kwon, Cheonan-Si (KR);
Bong-Sang Lee, Suwon-si (KR);
Su-Jun Park, Yongin-si (KR);
Bong-Geun Cha, Hwaseong-Si (KR);
Jun-Ki Kim, Chungcheongbuk-do (KR); Jiyeong Han, Ulsan (KR);
Myeongcheol Kil, Iksan-Si (KR)

(73) Assignee: CTC BIO, INC., Seoul (KR)

( * ) Notice: Subject to any disclaimer, the term of this patent is extended or adjusted under 35 U.S.C. 154(b) by 0 days.

(21) Appl. No.: 17/017,915

(22) Filed: Sep. 11, 2020

(65) Prior Publication Data

US 2020/0405714 A1    Dec. 31, 2020

Related U.S. Application Data

(63) Continuation-in-part of application No. 16/688,515, filed on Nov. 19, 2019, now abandoned, which is a continuation of application No. 14/783,670, filed as application No. PCT/KR2014/003160 on Apr. 11, 2014, now abandoned.

(30) Foreign Application Priority Data

Apr. 11, 2013 (KR) .................. 10-2013-0040084

(51) Int. Cl.
*A61K 31/4985* (2006.01)
*A61K 9/70* (2006.01)
*A61K 47/38* (2006.01)
*A61K 47/10* (2017.01)
*A61K 47/36* (2006.01)
*A61K 9/00* (2006.01)
*A61K 47/32* (2006.01)
*A61K 47/34* (2017.01)

(52) U.S. Cl.
CPC ........ *A61K 31/4985* (2013.01); *A61K 9/0056* (2013.01); *A61K 9/7007* (2013.01); *A61K 47/10* (2013.01); *A61K 47/32* (2013.01); *A61K 47/34* (2013.01); *A61K 47/36* (2013.01); *A61K 47/38* (2013.01); *A61K 9/006* (2013.01)

(58) Field of Classification Search
CPC .... A61K 9/0056; A61K 9/7007; A61K 47/36; A61K 47/38; A61K 1/4985; A61K 47/32; A61K 9/006; A61K 47/10; A61K 47/34
See application file for complete search history.

(56) References Cited

U.S. PATENT DOCUMENTS

| 2007/0104792 | A1 | 5/2007 | Jenkins |
| 2008/0194695 | A1 | 8/2008 | Jeon et al. |
| 2009/0047330 | A1* | 2/2009 | Bangalore ............ A61K 31/519 424/443 |
| 2009/0311325 | A1 | 12/2009 | Janssens et al. |
| 2010/0179159 | A1 | 7/2010 | Alles et al. |
| 2011/0136814 | A1* | 6/2011 | Andrews ................... A61P 9/12 514/248 |
| 2011/0136815 | A1 | 6/2011 | Zerbe et al. |
| 2011/0263606 | A1 | 10/2011 | Zerbe et al. |
| 2013/0323307 | A1 | 12/2013 | Jeon et al. |
| 2013/0345150 | A1* | 12/2013 | Steele .................... A61P 27/02 514/20.5 |

FOREIGN PATENT DOCUMENTS

| CN | 102824333 A | 12/2012 |
| EP | 2698147 A1 | 2/2014 |
| JP | 2005-511522 A | 4/2005 |
| JP | 2008-517935 A | 5/2008 |
| KR | 10-0627687 B1 | 9/2006 |
| KR | 10-2008-0023873 A | 3/2008 |
| KR | 10-2011-0041412 A | 4/2011 |
| WO | WO-2003/030882 A1 | 4/2003 |
| WO | WO-2006/047365 A1 | 5/2006 |
| WO | WO-2012/053006 A2 | 4/2012 |
| WO | WO-2012/108738 A2 | 8/2012 |

OTHER PUBLICATIONS

International Search Report for Application No. PCT/KR2014/003160, dated Aug. 26, 2014.
Office Action (Non-final) dated Mar. 5, 2018 from corresponding U.S. Appl. No. 14/783,670.
Office Action (Non-final) dated Apr. 21, 2017 from corresponding U.S. Appl. No. 14/783,670.
Office Action (Non-final) dated May 25, 2016 from corresponding U.S. Appl. No. 14/783,670.

(Continued)

*Primary Examiner* — Jianfeng Song
(74) *Attorney, Agent, or Firm* — Harness, Dickey & Pierce, P.L.C.

(57) ABSTRACT

The present disclosure relates to a film formulation for oral administration, containing tadalafil free base and a method of preparing the same, and a film may be provided with maximized dispersion stability of tadalafil free base in the film by the addition of a dispersion stabilizing agent in small amounts without unique fragrance or favor that may appear when other dispersion stabilizing agents known in the art are used, and an extremely low likelihood that a reagglomeration phenomenon of tadalafil free base particles will occur, and an amount of bubbles generated may be significantly reduced during a production process.

14 Claims, No Drawings

(56) References Cited

OTHER PUBLICATIONS

Office Action (Final) dated Jul. 3, 2018 from corresponding U.S. Appl. No. 14/783,670.
Office Action (Final) dated Sep. 7, 2017 from corresponding U.S. Appl. No. 14/783,670.
Office Action (Final) dated Oct. 31, 2016 from corresponding U.S. Appl. No. 14/783,670.
Decision on Appeal dated Sep. 24, 2019 from corresponding U.S. Appl. No. 14/783,670.
Office Action (Non-Final) from corresponding U.S. Appl. No. 16/688,515, dated Jan. 31, 2020.
Office Action (Final) from corresponding U.S. Appl. No. 16/688,515, dated May 11, 2020.

* cited by examiner

TADALAFIL FREE BASE-CONTAINING FILM DOSAGE FORM CONTAINING POLYETHYLENE GLYCOL-BASED POLYMER AND/OR VINYL PYRROLIDONE-BASED POLYMER AS DISPERSION STABILIZER

CROSS-REFERENCE TO RELATED APPLICATIONS

The present application is a continuation in part of U.S. application Ser. No. 16/688,515, filed on Nov. 19, 2019, which is a continuation of Ser. No. 14/783,670, filed on Oct. 9, 2015, which is a National Phase entry of PCT/KR2014/003160, filed on Apr. 11, 2014, which claims priority to Korean Patent Application No. 10-2013-0040084 filed on Apr. 11, 2013, the disclosures of which are incorporated herein by references.

FIELD

The present disclosure relates to a film formulation containing tadalafil free base as an active ingredient and a method of preparing the same. More particularly, the present disclosure relates to a tadalafil free base-containing film with content uniformity and dispersion uniformity and a method of producing a tadalafil free base-containing film with content uniformity and dispersion uniformity.

BACKGROUND

An active ingredient of Cia tadalafil, has been used to treat male erectile dysfunction. Prescription information of Cialis® describes this product as almond-shaped tablets for oral administration, coated with a film containing tadalafil and the following inactive ingredients: croscarmellose sodium, hydroxypropyl cellulose, hypromellose, iron oxide, lactose monohydrate, magnesium stearate, microcrystalline cellulose, sodium lauryl sulfate, talc, titanium dioxide and triacetin (see pi.lilly.com/us/cialis-pi.pdf).

The chemical designation of tadalafil is (6R-trans)-6-(1,3-benzodioxol-5-yl)-2,3,6,7,12,12a-hexahydro-2-methylpyrazino[1',2':1,6]pyrido[3,4-b]indole-1,4-dione. Tadalafil (CAS #171596-29-5) has a structure represented as below:

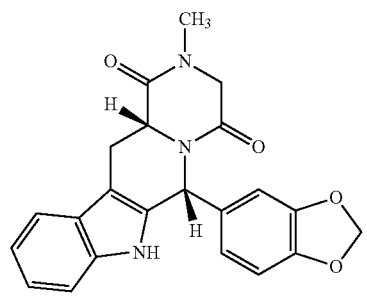 [SMILES: CN1CC(=O)N2[C@H](c3ccc4c(c3)OCO4)c3[nH]c4ccccc4c3C[C@@H]2C1=O]

Tadalafil is a solid that is practically insoluble in water, and is known as being slightly soluble in some organic solvents such as methanol, ethanol and acetone. U.S. Pat. No. 6,841,167 discloses "having a water solubility of about 2 μg per 1 milliliter (mL) of water at 25° C.".

When tadalafil is produced in an insufficient dissolved state or in a dispersed or suspended state, a layer separation of a film preparing solution and non-uniformity of an active ingredient may occur due to strong water repellency. Such layer separation and non-uniformity takes place in processes of preparing the film preparing solution, and delivering for coating of the film preparing solution, and drying after coating.

In an attempt to overcome poor water solubility resulting from strong hydrophobicity of tadalafil, many technologies were applied. U.S. Pat. No. 6,841,167 reports a pharmaceutical formulation containing a mixture of tadalafil in "a free drug" form with a diluent, a lubricant, a hydrophilic binder and disintegrant. Also, U.S. Pat. No. 6,821,975 discloses "a free drug particulate" form of tadalafil "comprising particles of a compound wherein at least 90% of the particles have a particle size of less than about 40 microns", limiting a particle size of tadalafil.

However, these methods all focus on improvement in solubility of tadalafil, and there is a need for an attempt to overcome strong hydrophobic properties of tadalafil.

SUMMARY

Technical Problem

The present disclosure is directed to providing a tadalafil free base-containing film preparing solution in which a dispersion stabilizing agent is present in a smaller amount than a compound conventionally used as a dispersion stabilizing agent, the dispersion stabilizing agent selected to allow uniform dispersion in a film without a reagglomeration phenomenon, rather than substantially dissolving tadalafil free base, and a film, and a method of preparing a tadalafil free base-containing film using the dispersion stabilizing agent.

Technical Solution

To achieve the object, the present disclosure provides a tadalafil free base-containing film in which a polyethylene glycol-based polymer, a vinylpyrrolidone-based polymer, or mixtures thereof is included in a tadalafil free base-containing film formulation as a dispersion stabilizing agent, and its film preparing solution, and their preparing methods.

More particularly, the present disclosure provides a tadalafil free base-containing film in which a film formulation includes tadalafil free base as an active ingredient, and a polyethyleneglycol-based polymer, a vinylpyrrolidone-based polymer, or mixtures thereof as a dispersion stabilizing agent.

Also, the present disclosure provides a tadalafil free base-containing film preparing solution including a tadalafil free base as an active ingredient, and a polyethyleneglycol-based polymer, a vinylpyrrolidone-based polymer, or mixtures thereof as a dispersion stabilizing agent.

Tadalafil free base is very difficult to prepare a film in an aqueous solution state due to strong hydrophobicity. Therefore, instead of overcoming strong hydrophobicity of tadalafil free base, the present disclosure is intended to make use of it. The present disclosure is based on findings that a film containing a desired content of tadalafil free base with a thickness and a size suitable for individual dose adaptation as well as desired properties may be obtained by dispersing (or suspending) tadalafil free base in a polymer solution based on strong hydrophobicity of tadalafil free base, rather than substantially dissolving tadalafil free base in a polymer solution.

In particular, when a polyethyleneglycol-based polymer, a vinylpyrrolidone-based polymer, or mixtures thereof is used as the dispersion stabilizing agent to disperse (or suspend)

tadalafil free base, even a small amount may maximize dispersion stability of tadalafil free base in a film and eliminate or reduce the likelihood that a reagglomeration phenomenon of tadalafil free base particles will occur after a film preparing solution is prepared, as well as significantly reducing an amount of bubbles generated during a production process. Further, the present disclosure is based on findings that excellence consists in being free of unique fragrance or favor appearing when other dispersion stabilizing agents (and/or surfactants) known in the art, for example, sodium lauryl sulfates (SLS) are used.

In the present disclosure, the film may be also called a strip, an orally dissolving film (ODF), or an orally disintegrating film (ODF), and represents a formulation that is adhered to and dissolves in the oral cavity, to be exact, on the tongue or the oral mucosa membrane, or under the tongue. The film formulation according to the present disclosure has advantages of taking a dose without drinking water and being convenient to carry with.

As used herein, "dispersing (or suspending) rather than substantially dissolving" represents that 15 wt % or less, preferably 10 wt % or less, more preferably 7 wt % or less, even more preferably 4 wt % or less, most preferably 2 wt % or less of the total tadalafil free base is dissolved in the polymer solution.

In the film formulation according to the present disclosure, because tadalafil free base does not substantially dissolve, it does not interact with a film forming polymer, and it is predicted that this is as one of the factors causing the resulting film to exhibit desirable properties, but the present disclosure is not limited to this theory.

In the present disclosure, it is characterized in that a polyethyleneglycol-based polymer and/or a vinylpyrrolidone-based polymer is used as the dispersion stabilizing agent to uniformly disperse tadalafil free base in the film. When a polyethyleneglycol-based polymer and/or vinylpyrrolidone-based polymer is used as the dispersion stabilizing agent, not only are there effects of maximizing the dispersion stability in the film while not dissolving tadalafil free base, but also eliminating or reducing the likelihood that a reagglomeration phenomenon of tadalafil particles will occur after a film solution is prepared.

In the present disclosure, the polyethyleneglycol-based polymer represents a homopolymer or a copolymer of a monomer expressed by the following chemical formula 1:

[Chemical formula 1]

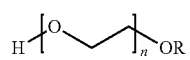

where R is hydrogen or an alkyl group having 1-6 carbon atoms, and the alkyl group represents linear or branched saturated lower aliphatic hydrocarbon, for example, methyl, ethyl, n-propyl, isopropyl, n-butyl, s-butyl, isobutyl, t-butyl and n-pentyl groups, and most preferably, R is hydrogen. When R is hydrogen in the above formula, the monomer expressed by the above chemical formula is polyethylene glycol (PEG).

The 'n' is an integer of from 1 to 300, preferably from 5 to 100, more preferably from 10 to 50, and most preferably from 11 to 35.

The homopolymer of the monomer expressed by the above chemical formula 1 represents a polymer formed from the monomer expressed by the above chemical formula 1 alone, and the copolymer of the monomer expressed by the above chemical formula 1 represents a polymer consisting of the monomer expressed by the above chemical formula 1 and other monomer that can be copolymerized with the monomer.

In the present disclosure, the monomer expressed by the above chemical formula 1 and other desirable monomer that can be copolymerized with the monomer include vinyl alcohol-based, and the vinyl alcohol-based polymer includes, for example, polyvinyl alcohol, polyvinyl acetate, ethylene vinyl alcohol, most preferably polyvinyl alcohol.

In the present disclosure, a most preferable example of the monomer expressed by the above chemical formula 1 is polyethylene glycol, and in this case, the polyethyleneglycol-based polymer may be a polyethylene glycol homopolymer or a polyethylene glycol copolymer. Also, a most preferable example of the polyethylene glycol copolymer is polyvinyl alcohol-polyethylene glycol.

The polyethyleneglycol-based polymer may have a molecular weight in the range between 200 g/mol and 10,000,000 g/mol, but in the case of a homopolymer, the molecular weight may be preferably between 200 g/mol and 35,000 g/mol, more preferably between 200 g/mol and 10,000 g/mol, and most preferably between 200 g/mol and 600 g/mol. When the polyethyleneglycol-based polymer having the molecular weight of less than 200 g/mol or more than 35,000 g/mol is used, it is difficult to maximize the dispersion stability of tadalafil free base, and the likelihood of reagglomeration will occur is high. For example, according to a particular embodiment, where polyethyleneoxide (PEO) having a chemical structure similar to the polyethyleneglycol-based polymer but a relatively high molecular weight is used as the dispersion stabilizing agent, it is impossible to disperse tadalafil free base stably and effectively, as opposed to the case where the polyethyleneglycol-based polymer is used as the dispersion stabilizing agent.

The polyethyleneglycol-based polymer exists as a liquid or solid at room condition (25° C.), and when the molecular weight is higher than or equal to 700 g/mol, it exists as a solid in flakes or powder form at room condition (25° C.) and the melting point increases in proportion to the molecular weight, and when the molecular weight is less than 700 g/mol, it exists as a liquid at room condition (25° C.). For the polyethyleneglycol-based polymer, in the present disclosure, a liquid polyethyleneglycol-based polymer is preferably used as the dispersion stabilizing agent, and a solid polyethyleneglycol-based polymer may be used after it becomes a liquid by heating at the temperature higher than or equal to the melting point. The polyethyleneglycol-based polymer in a liquid state or changed to a liquid state may uniformly disperse tadalafil free base in an aqueous solution without a separate organic solvent.

In the present disclosure, the vinylpyrrolidone-based polymer represents a homopolymer or a copolymer containing N-vinyl-2-pyrrolidone as a monomer. The vinylpyrrolidone homopolymer represents a polymer formed from N-vinyl-2-pyrrolidone alone, and the vinylpyrrolidone copolymer represents a polymer consisting of N-vinyl-2-pyrrolidone and other monomer that can be copolymerized with N-vinyl-2-pyrrolidone.

In the present disclosure, other monomer that can be copolymerized with N-vinyl-2-pyrrolidone is a vinyl acetate-based polymer, and the vinyl acetate-based polymer is most preferably vinyl acetate.

In the present disclosure, the vinylpyrrolidone-based polymer preferably includes, for example, polyvinylpyrrolidone or a vinylpyrrolidone-vinyl acetate copolymer.

In the present disclosure, the dispersion stabilizing agent may be present in an amount of from 0.2 wt % to 20 wt %, or from 0.2 wt % to 10 wt %, more preferably from 0.5 wt % to 5 wt %, and most preferably from 1 wt % to 5 wt % based on the total weight of the dried film. For example, when the vinylpyrrolidone-based polymer and/or the polyethyleneglycol-based polymer as the dispersion stabilizing agent is present less than 0.2 wt %, a reagglomeration phenomenon of tadalafil free base particles occurs in the resulting film and uniform dispersion of tadalafil free base is impossible, and when the vinylpyrrolidone-based polymer and/or the polyethyleneglycol-based polymer as the dispersion stabilizing agent is present more than 10 wt %, it is uneconomical and unique flavor and fragrance may appear by the addition of an excessive amount of the dispersion stabilizing agent.

In the present disclosure, by the use of the dispersion stabilizing agent, an amount of other additives used may be reduced, for example, additives added to disperse tadalafil free base between polymer chains more stably beyond the simple suspension of free base of tadalafil in the polymer solution, to reduce agglomeration of tadalafil free base particles, or to inhibit layer separation. For example, the total amount of a dispersion stabilizing agent, a plasticizer, and a surfactant necessary to prepare the film may be reduced.

In the present disclosure, the film preferably comprises glycerin as a plasticizer. The content of glycerin may be from 3 wt % to 20 wt %, more preferably from 5 wt % to 15 wt %, and most preferably from 8 wt % to 13 wt % based on the total weight of the dried film. In other embodiment, the film may comprise other plasticizer like propylene glycol in addition to the glycerin.

The total content of the dispersion stabilizing agent, the plasticizer, and the surfactant may be from 1 wt % to 90 wt %, more preferably from 1 wt % to 70 wt %, even more preferably from 1 wt % to 50 wt %, and most preferably from 10 wt % to 15 wt % based on the total weight of the dried film. Also, the content of the the dispersion stabilizing agent may be from 5 wt % to 90 wt %, most preferably from 10 wt % to 20 wt % based on the total weight of the surfactant, the plasticizer, and the dispersion stabilizing agent used to prepare the film. When the content is less than 5 wt % or more than 90 wt %, it is difficult to stably disperse tadalafil free base. The plasticizer included in the film preparing solution according to the present disclosure includes, but is not limited to, for example, glycerin, sorbitol, propylene glycol, or mixtures thereof.

The film may optionally further comprise a surfactant which may include, but are not limited to, for example, polysorbate, polyoxyethylenealkylether, polyoxyethylene castor oil, polyoxyethylenestearate, docusate sodium, sodium lauryl sulfate, sorbitan ester, or mixtures thereof. The total content of the surfactant may be from 0.1 wt % to 3 wt %, more preferably from 0.3 wt % to 2 wt %, and most preferably from 0.5 wt % to 1.5 wt % based on the total weight of the dried film.

The present disclosure is characterized by preparing a film formulation with maximized dispersion stability by dispersing (suspending) tadalafil free base in the polymer solution based on strong hydrophobicity of tadalafil free base rather than substantially dissolving tadalafil free base in the polymer solution. Thus, preferably 90 wt % or more, more preferably 95 wt % or more, and even more preferably 98 wt % or more of a solvent is water to keep tadalafil free base from being dissolved. Taking into account various aspects such as a thickness and a drying rate of the film when applying the film preparing solution, and viscosity of the film preparing solution, an amount of solvents used in producing the film is preferably from 0.7 parts by weight to 4 parts by weight, more preferably from 1.3 parts by weight to 3.3 parts by weight, per 1 part by weight of film constituent materials remaining after drying.

As the polymer used to form the film used in the present disclosure, for the purpose of the present disclosure, it is more preferred to use a polymer having viscosity of 15 cp or less (preferably between 1 cp and 15 cp) as measured in a 2 wt % aqueous solution. That is, when this polymer is used, it is more preferred in terms of a production process as previously noted and the properties of the resulting film, and besides, there is an advantage of rapid disintegration in the oral cavity. The total content of hydroxypropyl cellulose may be from 20 wt % to 80 wt %, more preferably from 40 wt % to 70 wt %, and most preferably from 45 wt % to 60 wt % based on the total weight of the dried film. More preferably, an example of the polymer of 15 cp or less includes pullulan, low density hydroxypropyl cellulose, low density hydroxypropyl methylcellulose.

However, for another purpose of the present disclosure (for example, to increase the strength of the film), it is more preferred to use a small amount of a high viscosity polymer having viscosity of 50 cp or more (preferably between 50 cp and 10,000 cp) as measured in a 2 wt % aqueous solution (together with the polymer of 15 cp or less), and in this case, the content of the high viscosity polymer of 50 cp or more is preferably 20 wt % or less, preferably 10 wt % or less, more preferably 5 wt % or less, even more preferably 3 wt % or less, and most preferably 1 wt % or less per the total weight of the film after drying. More preferably, an example of the polymer of 50 cp or more includes xanthan gum, propylene glycol alginate, sodium alginate, alginic acid, hydroxypropyl methylcellulose, hydroxypropyl cellulose, guar gum, and carboxymethyl cellulose sodium. The polymer used for forming the film in the present disclosure includes, but is not limited to, for example, pullulan, hydroxypropyl cellulose, hydroxypropyl methylcellulose, xanthan gum, pullulan, sodium alginate, propylene glycol alginate, povidone, poloxamer, polyvinylalcohol, alginic acid, carrageenan, carbomer, carboxymethyl cellulose calcium, carboxymethyl cellulose sodium, gelatin, or mixtures thereof.

Therefore, as a particular embodiment, the present disclosure provides a film or a film preparing solution including tadalafil free base a dispersion stabilizing agent, hydroxypropyl cellulose, and glycerin and by this combination, the objects of the present disclosure may be achieved more effectively. More preferably, the present disclosure provides a film including 10 wt % to 30 wt % of tadalafil free base, 0.2 wt % to 50 wt % of the dispersion stabilizing agent, 20 wt % to 80 wt % of hydroxypropyl cellulose, and 5 wt % to 15 wt % of glycerin based on the total weight of the dried film.

Also, in the present disclosure, the film preparing solution may optionally further include a sweetening agent, a fragrance, a defoaming agent or a coloring agent.

In the present disclosure, the sweetening agent may be at least one selected from the group consisting of mannitol, sorbitol, xylitol, sucralose, aspartame, stevioside, and neohesperidin. Preferably, the sweetening agent may be mannitol or a combination of mannitol and other sweetening agent(s). The content of the sweetening agent may be from 3 wt % to 20 wt %, and more preferably from 5 wt % to 15 wt %, and most preferably from 5 wt % to 12 wt % based on the total weight of the dried film.

In the present disclosure, the coloring agent may be at least one selected from the group consisting of titanium oxide, talc, and ferric oxide pigments. Preferably, the coloring agent comprises titanium oxide. That is, the coloring agent may be titanium dioxide or a combination of titanium dioxide and other coloring agent(s). The content of the titanium oxide may be from 3 wt % to 20 wt %, and more preferably from 5 wt % to 17 wt %, and most preferably from 5 wt % to 12 wt % based on the total weight of the dried film. The content of the ferric oxide pigments may be from 0.1 wt % to 2 wt %, and more preferably from 0.2 wt % to 1 wt %, and most preferably from 0.2 wt % to 0.7 wt % based on the total weight of the dried film. The total content of the coloring agent may be from 3 wt % to 22 wt %, and more preferably from 5 wt % to 19 wt %, and most preferably from 5 wt % to 13 wt % based on the total weight of the dried film.

In the present disclosure, the defoaming agent may be at least one selected from the group consisting of simethicone and dimethicone. An emulsion type of simethicone or dimethicone may be used. Preferably, the defoaming agent may be simethicone. The content of the defoaming agent may be from 0.001 wt % to 1 wt %, and more preferably from 0.005 wt % to 0.5 wt %, and most preferably from 0.01 wt % to 0.1 wt % based on the total weight of the dried film. When an emulsion is used as the defoaming agent, the content is calculated based on the simethicone or dimethicone only except other ingredients in the emulsion.

The present disclosure provides a method of producing a tadalafil free base-containing film by which a tadalafil free base-containing film is produced by drying a polymer solution having tadalafil free base dispersed therein by the addition of a dispersion stabilizing agent.

The film according to the present disclosure may be produced by drying the polymer solution in which tadalafil free base is dispersed by the addition of the vinylpyrrolidone-based polymer and/or the polyethyleneglycol-based polymer as the dispersion stabilizing agent. More preferably, the film is produced by drying the film preparing solution containing dissolved polymer according to the present disclosure in which water more than or equal to 90 wt % of a solvent is used and 10 wt % to 30 wt % of tadalafil free base is dispersed using 0.2 wt % to 20 wt % of the dispersion stabilizing agent based on the total weight of the dried film, and the content of the polymer may be from 20 wt % to 80 wt % per the total weight of the dried film. Even more preferably, the film according to the present disclosure may additionally include a plasticizer, a surfactant and/or a dispersion stabilizing agent as well as the vinylpyrrolidone-based polymer and/or polyethyleneglycol-based polymer dispersion stabilizing agent, and the total content of the vinylpyrrolidone-based polymer and/or polyethyleneglycol-based polymer dispersion stabilizing agent, and the plasticizer, the surfactant, and/or the dispersion stabilizing agent may be from 1 wt % to 90 wt % based on the total weight of the dried film.

The film according to the present disclosure may be produced by a method comprising:

adding a tadalafil free base, a dispersion stabilizing agent, a film-forming polymer, a plasticizer, and optionally a surfactant, a sweetening agent, a coloring agent, a fragrance, a defoaming agent, or mixtures thereof to water, to prepare a polymer solution; and drying the polymer solution in which the tadalafil free base is dispersed and 2 wt % or less of the total free base is dissolved, wherein the dispersion stabilizing agent is selected from a polyvinyl alcohol-polyethylene glycol copolymer, a polyethylene glycol, a polyvinylpyrrolidone, a vinylpyrrolidone-vinyl acetate copolymer or mixtures thereof, wherein the film-forming polymer has a content of 40 wt % to 70 wt % based on a total weight of the dried film and comprises hydroxypropyl cellulose, wherein the plasticizer is glycerin, wherein the tadalafil free base is stably dispersed in the tadalafil free base-containing film, wherein the film comprises 10 wt % to 30 wt % of the tadalafil free base, 0.2 wt % to 5 wt % of the dispersion stabilizing agent, and 5 wt % to 15 wt % of glycerin, and wherein 95 wt % or more of a solvent that is used in producing the film is water.

In the method above, the dispersion stabilizing agent, the film-forming polymer, the plasticizer, the surfactant, the sweetening agent, the coloring agent, the fragrance, and the defoaming agent are as mentioned in the description of the film.

Advantageous Effects

According to the present disclosure, a film may be provided with maximized dispersion stability of tadalafil free base in the film by the addition of a small amount of a polyethyleneglycol-based polymer as a dispersion stabilizing agent without unique fragrance or favor that may appear when other dispersion stabilizing agents known in the art are used, and an extremely low likelihood that a reagglomeration phenomenon of tadalafil free base particles will occur, and an amount of bubbles generated may be significantly reduced during a production process.

DETAILED DESCRIPTION

Hereinafter, the embodiments of the present disclosure will be described in detail to assist the understanding of the present disclosure. The present disclosure may, however, be embodied in different forms and should not be construed as limited to the embodiments set forth below. Rather, these embodiments are provided so that this disclosure will fully convey the scope of the present disclosure to one of ordinary skill in the art.

<Preparation of a Tadalafil Free Base-Containing Film Formulation>

A tadalafil free base-containing film formulation was prepared as follows. A plasticizer, an additive, a sweeting agent, a surfactant, and a dispersion stabilizing agent were added to purified water, and agitated to dissolve or disperse in the purified water, and tadalafil free base was added thereto. Subsequently, homogenization was performed using a homogenizer (Ultra turrax T-25, IKA). A polymer was added thereto, and homogenization was performed using the same homogenizer. Subsequently, gas was removed from the film preparing solution at 45° C. under a vacuum condition, and after cooling to room temperature, coating was performed with an optimum thickness on a polyethylene (PE) film. Subsequently, drying was performed at 80° C. to prepare a film formulation containing tadalafil free base.

Test Examples 1-14. Comparison of Dispersion Stability Based on a Type of a Dispersion Stabilizing Agent Added A film was produced by the same method as that of the above described "preparation of a tadalafil free base-containing film formulation", varying the ingredients included in the film and their content as shown in the following table 1, and a result of measuring dispersion stability of tadalafil free base in the film was indicated in RSD % (relative standard deviation).

RSD % was determined by cutting the resulting bulk film to predetermined size and area, and measuring how uniformly tadalafil free base is distributed through analysis of the content of tadalafil free base included in each tailored film.

As a result, as can be seen in the above table 1, when a polyethyleneglycol-based polymer was included as a dispersion stabilizing agent, good dispersion stability was exhibited, and when polyethylene glycol was used as a dispersion stabilizing agent (Example 4), RSD % was found to be 0.5, and when a polyvinyl alcohol-polyethylene glycol copolymer was used as a dispersion stabilizing agent (Example 7), RSD % was found to be 0.9. Also, when a vinylpyrrolidone-based polymer was used as a dispersion stabilizing agent, good dispersion stability was exhibited, and when polyvinylpyrrolidone was used as a dispersion stabilizing agent (Example 6), RSD % was found to be 0.9, and when a vinylpyrrolidone-vinyl acetate copolymer was used as a dispersion stabilizing agent (Example 13), RSD % was found to be 1.1. These results show significant lower RSD % than the case where a dispersion stabilizing agent is not included (i.e., Comparative examples 1-3) and the case where compounds other than a polyethyleneglycol-based polymer or a vinylpyrrolidone-based polymer are included as a dispersion stabilizing agent (i.e., Examples 5, 8-12, 14). Thus, when a polyethyleneglycol-based polymer or a vinylpyrrolidone-based polymer is used as a dispersion stabilizing agent, it results in stable dispersion of tadalafil free base in a film and consequential good stability, from which it is expected that a layer separation or a progressive reagglomeration phenomenon will not occur.

Tables 2 and 3 describe Examples 101-112, including the respective RSD values (an average of 10 individual films in each example). The films of Examples 101-112 were prepared the same as those described in the example above.

TABLE 1

| | Comparative Example | | | Example | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Tadalafil | 17.1 | 17.1 | 17.1 | 16.7 | 16.7 | 16.7 | 16.7 | 16.7 | 16.7 | 16.7 | 16.7 | 16.7 | 16.7 | 16.7 |
| Hydroxypropyl cellulose | 43.0 | 60.2 | 53.0 | 51.8 | 51.8 | 51.8 | 51.8 | 51.8 | 51.8 | 51.8 | 51.8 | 51.8 | 51.8 | 51.8 |
| Polyethylene glycol | | | | 2.5 | | | | | | | | | | |
| Polyethylene oxide | | | | | 2.5 | | | | | | | | | |
| Polyvinylpyrrolidone (Povidone) | | | | | | 2.5 | | | | | | | | |
| Polyvinylalcohol-polyethylene glycol copolymer | | | | | | | 2.5 | | | | | | | |
| Hydroxyethyl cellulose | | | | | | | | 2.5 | | | | | | |
| Hydroxyethylmethcyl cellulose | | | | | | | | | 2.5 | | | | | |
| Polyoxyethylene caster oil | | | | | | | | | | 2.5 | | | | |
| Polyoxyethylene stearate | | | | | | | | | | | 2.5 | | | |
| Triethyl citrate | | | | | | | | | | | | 2.5 | | |
| Vinylpyrrolidone-vinylacetate copolymer | | | | | | | | | | | | | 2.5 | |
| Polyoxyethylene alkyl ether | | | | | | | | | | | | | | 2.5 |
| Glycerin | 11.2 | 11.2 | 11.2 | 10.9 | 10.9 | 10.9 | 10.9 | 10.9 | 10.9 | 10.9 | 10.9 | 10.9 | 10.9 | 10.9 |
| Titanium oxide | 21.9 | 9.7 | 13.1 | 16.3 | 16.3 | 16.3 | 16.3 | 16.3 | 16.3 | 16.3 | 16.3 | 16.3 | 16.3 | 16.3 |
| Sucralose | 1.0 | 1.0 | 1.1 | 1.0 | 1.0 | 1.0 | 1.0 | 1.0 | 1.0 | 1.0 | 1.0 | 1.0 | 1.0 | 1.0 |
| Polysorbate 80 | 5.8 | 0.8 | 4.5 | 0.8 | 0.8 | 0.8 | 0.8 | 0.8 | 0.8 | 0.8 | 0.8 | 0.8 | 0.8 | 0.8 |
| Total | 100.0 | 100.0 | 100.0 | 100.0 | 100.0 | 100.0 | 100.0 | 100.0 | 100.0 | 100.0 | 100.0 | 100.0 | 100.0 | 100.0 |
| Content RSD % | 3.9 | 4.3 | 4.5 | 0.5 | 3.9 | 0.9 | 0.9 | 3.7 | 3.2 | 2.9 | 3.2 | 2.9 | 1.1 | 4.0 |
| Solvent | | | | | | | to 100% | | | | | | | |

TABLE 2

| (Ingredient: wt %/film) | Example 101 | Example 102 | Example 103 | Example 104 | Example 105 | Example 106 |
|---|---|---|---|---|---|---|
| Tadalafil | 16.6 | 10 | 30 | 25 | 12 | 25 |
| Hydroxypropylcellulose | 51.58 | 65.32 | 44.98 | 39.63 | 69.91 | 40.12 |
| Xanthan gum | 0.2 | 0.1 | 0.3 | 3 | 0.01 | 3 |
| Glycerin | 10.8 | 12 | 6.5 | 12 | 5 | 15 |
| Polyethylene glycol 400 | 2.5 | 1.5 | 4.5 | 3 | 0.5 | 2 |
| Mannitol | 8.3 | 3 | 4 | 2.3 | 3 | 8.2 |
| Simethicone emulsion (30%)* | 0.02 | 0.02 | 0.02 | 0.02 | 0.02 | 0.02 |
| Titanium dioxide | 7.5 | 5 | 7.5 | 12 | 5 | 5 |
| Polysorbate 80 | 0.8 | 1.5 | 0.5 | 1 | 3 | 0.1 |
| Sucralose | 0.7 | 0.7 | 0.7 | 0.7 | 0.7 | 0.7 |
| Ferric oxide (Yellow) | 0.1 | 0.06 | 0.1 | 0.15 | 0.06 | 0.06 |
| Kollicoat IR sunset yellow | 0.6 | 0.5 | 0.6 | 0.9 | 0.5 | 0.5 |
| Vanilla flavour powder | 0.3 | 0.3 | 0.3 | 0.3 | 0.3 | 0.3 |
| Water | q.s. | q.s. | q.s. | q.s. | q.s. | q.s. |
| Total | 100 | 100 | 100 | 100 | 100 | 100 |
| RSD | 0.39 | 0.68 | 0.45 | 0.39 | 0.81 | 0.53 |

*0.07 mg of Simethicone emulsion was evaporated during process.

TABLE 3

| (Ingredient: wt %/film) | Example 107 | Example 108 | Example 109 | Example 110 | Example 111 | Example 112 |
|---|---|---|---|---|---|---|
| Tadalafil | 10 | 10 | 15 | 20 | 10 | 10 |
| Hydroxypropylcellulose | 69.91 | 47.42 | 47.08 | 49.98 | 69.92 | 69.93 |
| Xanthan gum | 0.01 | 0.5 | 0.2 | 0.2 | 0 | 0.01 |
| Glycerin | 5 | 15 | 10 | 8 | 5 | 5 |
| Polyethylene glycol 400 | 2.5 | 0.2 | 2 | 5 | 2.5 | 2.5 |
| Mannitol | 3 | 20 | 15 | 5.6 | 3 | 3 |
| Simethicone emulsion (30%)* | 0.02 | 0.02 | 0.02 | 0.02 | 0.02 | 0 |
| Titanium dioxide | 5 | 5 | 7.5 | 7.5 | 5 | 5 |
| Polysorbate 80 | 3 | 0.3 | 1.5 | 2 | 3 | 3 |
| Sucralose | 0.7 | 0.7 | 0.7 | 0.7 | 0.7 | 0.7 |
| Ferric oxide (Yellow) | 0.06 | 0.06 | 0.1 | 0.1 | 0.06 | 0.06 |
| Kollicoat IR sunset yellow | 0.5 | 0.5 | 0.6 | 0.6 | 0.5 | 0.5 |
| Vanilla flavour powder | 0.3 | 0.3 | 0.3 | 0.3 | 0.3 | 0.3 |
| Water | q.s. | q.s. | q.s. | q.s. | q.s. | q.s. |
| Total | 100 | 100 | 100 | 100 | 100 | 100 |
| RSD | 0.43 | 0.95 | 0.52 | 0.33 | 0.37 | 0.43 |

*0.07 mg of Simethicone emulsion was evaporated during process.

INDUSTRIAL APPLICABILITY

According to the present disclosure, a film may be provided with maximized dispersion stability of tadalafil free base in the film by the addition of a small amount of a polyethyleneglycol-based polymer as a dispersion stabilizing agent without unique fragrance or favor that may appear when other dispersion stabilizing agents known in the art are used, and an extremely low likelihood that a reagglomeration phenomenon of tadalafil free base particles will occur, and an amount of bubbles generated may be significantly reduced during a production process.

What is claimed is:

1. A method of preparing a tadalafil free base-containing film, comprising:
   adding a tadalafil free base, a dispersion stabilizing agent, a film-forming polymer, a plasticizer, a polysorbate 80, titanium dioxide, mixtures thereof to water, to prepare a polymer solution; and
   drying the polymer solution in which the tadalafil free base is dispersed and 2 wt % or less of the total free base is dissolved,
   wherein the dispersion stabilizing agent is selected from a polyvinyl alcohol-polyethylene glycol copolymer, a polyethylene glycol, a polyvinylpyrrolidone, a vinylpyrrolidone-vinyl acetate copolymer or mixtures thereof,
   wherein the film-forming polymer has a content of 40 wt % to 70 wt % based on a total weight of the dried film and comprises hydroxypropyl cellulose,
   wherein the plasticizer is glycerin,
   wherein the tadalafil free base is stably dispersed in the tadalafil free base-containing film,
   wherein the film comprises 10 wt % to 30 wt % of the tadalafil free base, 0.2 wt % to 5 wt % of the dispersion stabilizing agent, 0.1 wt % to 3 wt % of the polysorbate 80, 5 wt % to 17 wt % of titanium dioxide, and 5 wt % to 15 wt % of glycerin, and
   wherein 90 wt % or more of a solvent that is used in producing the film is water.

2. The method of claim 1, wherein the film-forming polymer comprises a second polymer having a viscosity of 50 cp or more as measured in a 2 wt % aqueous solution, the second polymer having a content of 3 wt % or less based on a total weight of the dried film.

3. The method of claim 1, wherein the film comprises 2 wt % to 5 wt % of the dispersion stabilizing agent.

4. The method of claim 1, wherein 98 wt % or more of a solvent that is used in producing the film is water.

5. The method of claim 1, further comprising adding one or more of sweetening agent, coloring agent, fragrance, or defoaming agent.

6. The method of claim 5, wherein the sweetening agent is at least one selected from the group consisting of mannitol, sorbitol, xylitol, aspartame, stevioside, and neohesperidin.

7. The method of claim 6, wherein the sweetening agent comprises mannitol.

8. The method of claim 7, wherein the mannitol comprises 3 wt % to 20 wt %, based on the total weight of the dried film.

9. The method of claim 5, wherein the defoaming agent is simethicone, dimethicone, or mixtures thereof.

10. The method of claim 1, wherein the tadalafil free base-containing film comprises wherein the film comprises about 16.7 wt % tadalafil free base, about 2.5 wt % dispersion stabilizing agent, about 10.9 wt % glycerin, and about 0.8 wt % polysorbate 80.

11. The method of claim 10, wherein the dispersion stabilizing agent is polyethylene glycol.

12. The method of claim 10, wherein the dispersion stabilizing agent is polyvinylpyrrolidone.

13. The method of claim 10, wherein the dispersion stabilizing agent is polyvinylalcohol-polyethylene glycol copolymer.

14. The method of claim 10, wherein the dispersion stabilizing agent is vinylpyrrolidone-vinyl acetate copolymer.

* * * * *